US009631008B2

(12) United States Patent
Pompiati et al.

(10) Patent No.: US 9,631,008 B2
(45) Date of Patent: Apr. 25, 2017

(54) IMMUNOGLOBULIN PURIFICATION (75) Inventors: Marc Pompiati, Penzberg (DE); Andreas Schaubmar, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 691 days.

(21) Appl. No.: 13/141,306

(22) PCT Filed: Dec. 18, 2009

(86) PCT No.: PCT/EP2009/009157
§ 371 (c)(1),
(2), (4) Date: Jun. 21, 2011

(87) PCT Pub. No.: WO2010/072381
PCT Pub. Date: Jul. 1, 2010

(65) Prior Publication Data
US 2011/0257370 A1    Oct. 20, 2011

(30) Foreign Application Priority Data
Dec. 22, 2008 (EP) .................................... 08022236

(51) Int. Cl.
C07K 1/18       (2006.01)
C07K 16/28      (2006.01)
C07K 16/06      (2006.01)
A61K 39/395     (2006.01)

(52) U.S. Cl.
CPC ...... *C07K 16/065* (2013.01); *A61K 39/39591* (2013.01); *C07K 1/18* (2013.01); *C07K 16/2803* (2013.01); *C07K 16/2866* (2013.01)

(58) Field of Classification Search
None
See application file for complete search history.

(56) References Cited

U.S. PATENT DOCUMENTS

| | | | |
|---|---|---|---|
| 4,272,521 A | 6/1981 | Zuffi | |
| 4,604,208 A | 8/1986 | Chu et al. | |
| 4,983,722 A | 1/1991 | Bloom et al. | |
| 5,429,746 A | 7/1995 | Shadle et al. | |
| 6,177,548 B1* | 1/2001 | Wan et al. | 530/390.5 |
| 6,716,598 B2 | 4/2004 | Blank et al. | |
| 7,323,553 B2 | 1/2008 | Fahrner et al. | |
| 2003/0229212 A1 | 12/2003 | Fahrner et al. | |
| 2006/0030696 A1 | 2/2006 | Bonnerjea et al. | |
| 2006/0194953 A1 | 8/2006 | Bonnerjea et al. | |
| 2007/0082367 A1 | 4/2007 | Godavarti et al. | |
| 2007/0167612 A1* | 7/2007 | Hua Zhou | 530/387.1 |
| 2007/0292442 A1 | 12/2007 | Wan et al. | |
| 2008/0058507 A1 | 3/2008 | Liu et al. | |
| 2008/0193981 A1 | 8/2008 | Fahrner et al. | |
| 2008/0312425 A1 | 12/2008 | Bonnerjea et al. | |

FOREIGN PATENT DOCUMENTS

| | | |
|---|---|---|
| EP | 0246579 B1 | 8/1993 |
| EP | 0530447 | 10/1997 |
| EP | 1084136 | 8/2004 |
| EP | 08022236.7 | 12/2008 |
| WO | 89/05157 | 6/1989 |
| WO | 94/00561 | 1/1994 |
| WO | 95/16037 | 6/1995 |
| WO | 99/62936 | 12/1999 |
| WO | 03/040166 | 5/2003 |
| WO | 2004/024866 | 3/2004 |
| WO | 2004/076485 | 9/2004 |
| WO | 2006024497 A1 | 3/2006 |
| WO | 2006/099308 A2 | 9/2006 |
| WO | 2007108955 A1 | 9/2007 |
| WO | 2008/145351 A1 | 12/2008 |
| WO | 2010072381 A1 | 7/2010 |

OTHER PUBLICATIONS

Bird et al., "Single-Chain Antigen-Binding Proteins" *Science* 242:423-426 (Oct. 1988).
Danielsson et al., "One-step purification of monoclonal IgG antibodies from mouse ascites" *Journal of Immunological Methods* 115:79-88 (1988).
Hunkapiller et al., "The growing immunoglobulin gene superfamily" *Nature* 323:15-16 (1986).
Huston et al., "Protein Engineering of Antibody Binding Sites: Recovery of Specific Activity in an Anti-Digoxin Single-Chain Fv Analogue Produced in *Escherichia coli*" *Proc. Natl. Acad. Sci. USA* 85:5879-5883 (Aug. 1988).
Jiskoot, W., et al., "Two-step purification of a murine monoclonal antibody intended for therapeutic application in man—Optimisation of purification conditions and scaling up" *J. of Immunological Methods* 124:143-156 (1989).
Knudsen et al., "Membrane ion-exchange chromatography for process-scale antibody purification" *Journal of Chromatography* 907(1-2):145-154 (2001).
Lynch, Paul, et al., "System for Aggregate Removal from Affinity-Purified Therapeutic-Grade Antibody" *Genetic Engineering News* 17(19):17 (Nov. 1, 1997).
Mhatre et al., "Purification of antibody Fab fragments by cation-exchange chromatography and pH gradient elution" *Journal of Chromatography A* 707(2):225-231 (Jul. 21, 1995).
Necina et al., "Capture of human monoclonal antibodies from cell culture supernatant by ion exchange media exhibiting high charge density" *Biotechnology and Bioengineering* 60(6):589-698 (Dec. 20, 1998).

(Continued)

*Primary Examiner* — Daniel E Kolker
*Assistant Examiner* — James Rogers (57) ABSTRACT The current invention reports a method for purifying an immunoglobulin, wherein the method comprises applying an aqueous, buffered solution comprising an immunoglobulin in monomeric, in aggregated, and in fragmented form to an anion exchange chromatography material under conditions whereby the immunoglobulin in monomeric form does not bind to the anion exchange material, and recovering the immunoglobulin in monomeric form in the flow-through from the anion exchange chromatography material, whereby the buffered aqueous solution has a pH value of from 8.0 to 8.5. In one embodiment the anion exchange chromatography material is a membrane anion exchange chromatography material.

3 Claims, 8 Drawing Sheets (56) References Cited

OTHER PUBLICATIONS

Vijayalakshmi, M., "Antibody Purification Methods" *Applied Biochemistry and Biotechnology* 75:93-102 (1998).

Wang, C. et al., "Cored Anion-Exchange Chromatography Media for Antibody Flow-Through Purification" Journal of Chrom:74-84 (Apr. 2007).

Schwarz et al., "Effiziente Aufreinigung von monoklonalen Antikorpern" LaborPraxis:62-66 (Jun. 1997), Translation provided by applicant.

Fahrner et al. et al., "Industrial Purification of Pharmaceutical Antibodies: Development, Operation, and Validation of Chromatography Processes" Biotechnol Genet Eng 18:301-327 (2001).

Amersham Biosciences "1". Ion Exchange Chromatography & Chromatofocusing: Principles and Methods, AA edition, 2004.

Boschetti "Antibody Separation by Hydrophobic Charge Induction Chromatography" Trends in Biotechnology 20(8)(Aug. 2002).

DrugBank Database entry for Rituximab, 6 pgs. Jun. 3, 2005.

GE Healthcare, Application Note 28-9078-92 AD, first published Jan. 2007.

Gottschalk, U. Process Scale Purification of Antibodies. (Excerpt) John Wiley & Sons, Inc., Hoboken, NJ, 2009.

Huse et al., "Purification of Antibodies by Affinity Chromatography" Journal Biochemical and Biophysical Methods 51:217-231 (2002).

Johnson et al., "Rituximab: Mechanisms and Applications" British Journal of Cancer 85(11):1619-1623 (2001).

Kelley et al., "Weak Partitioning Chromatography for anion Exchange Purification of Monoclonal Antibodies" Biotechnology and Bioengineering 101(3)(Oct. 15, 2008).

"Molecular Weight and Isoelectric Point of Various Human Immunoglobulins" extract from Agrisera Antibodies, 1 pg.

Mora et al., "Disposable Membrane Chromatography: Performance Analysis and Economic Cost Model"BioProcess International: 38-42 (Jun. 2006).

Schwartz et al., "Comparison of Hydrophobic Charge Induction Chromatography with Affinity Chromatography on Protein A for Harvest and Purification of Antibodies" Journal of Chromatography A 908:251-263 (2001).

Shukla et al., "Strategies to Address Aggregation During Protein A Chromatography" BioProcess Technical:36-44 (May 2005).

Sigma-Aldrich—Capto™ Q Product Description, 2 pgs.

Sigma-Aldrich—Sepharose® Ion Exchange Media Product Information, 4 pgs.

Walsh, G. Proteins Biochemistry and Biotechnology. (Excerpt) 1st edition, John Wiley & Sons Ltd., West Sussex, 2002.

Zhou et al., "Membrane Chromatography as a Robust Purification System for Large-Scale Antibody Production" BioProcess International 3:32-37 (Sep. 2005).

Q Sepharose Fast Flow Data Shee, 1 page, Printed Oct. 9, 2014.

* cited by examiner

| Q-Membrane anti-CCR5 antibody | load | flow-through |
|---|---|---|
| pH 7.5 | 1.20% Aggregates | 0.76% Aggregates |
| pH 8.5 | 1.44% Aggregates | 0.37% Aggregates |
| | | |
| Q-Membrane anti-CD19 antibody | load | flow-through |
| pH 7.5 | 0.89% Aggregates | 0.41% Aggregates |
| pH 8.5 | 0.94% Aggregates | below detection limit |

IMMUNOGLOBULIN PURIFICATION

The current invention is in the field of purification of polypeptides. It is reported a method for providing an immunoglobulin in monomeric form by separating the immunoglobulin in solution from impurities, especially from the immunoglobulin in aggregated form and from immunoglobulin fragments.

BACKGROUND OF THE INVENTION

Proteins and especially immunoglobulins play an important role in today's medical portfolio. For human application every therapeutic protein has to meet distinct criteria. To ensure the safety of biopharmaceutical agents for humans, nucleic acids, viruses and host cell proteins, which could cause harm, have to be removed especially. To meet regulatory specifications one or more purification steps have to follow the fermentation process. Among other things, purity, throughput, and yield play an important role in determining an appropriate purification process.

Different methods are well established and widespread used for protein purification, such as affinity chromatography with microbial proteins (e.g. protein A or protein G affinity chromatography), ion exchange chromatography (e.g. cation exchange (sulfopropyl or carboxymethyl resins), anion exchange (amino ethyl resins) and mixed-mode ion exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (see e.g. Vijayalakshmi, M. A., Appl. Biochem. Biotech. 75 (1998) 93-102).

Necina, R., et al. (Biotechnol. Bioeng. 60 (1998) 689-698) reported the capture of human monoclonal antibodies directly from cell culture supernatants by ion exchange media exhibiting high charge density. In WO 89/05157 a method is reported for the purification of product immunoglobulins by directly subjecting the cell culture medium to a cation exchange treatment. A one-step purification of monoclonal IgG antibodies from mouse ascites is described by Danielsson, A., et al., J. Immunol. Meth. 115 (1988), 79-88.

Mhatre, R., et al., J. Chrom. A 707 (1995) 225-231, explored the purification of antibody Fab fragments by cation exchange chromatography and pH gradient elution. WO 94/00561 reports human monoclonal anti-rhesus antibodies and cell lines producing the same. A method for purifying a polypeptide by ion exchange chromatography is reported in WO 2004/024866 in which a gradient wash is used to resolve a polypeptide of interest from one or more contaminants. Schwarz, A., et al., Laborpraxis 21 (1997) 62-66, report the purification of monoclonal antibodies with a CM-HyperD-column. WO 2004/076485 reports a process for antibody purification by protein A and ion exchange chromatography. In EP 0 530 447 a process for purifying IgG monoclonal antibodies by a combination of three chromatographic steps is reported. The removal of protein A from antibody preparations is reported in U.S. Pat. No. 4,983,722.

Recombinant monoclonal antibody processes often employ anion-exchange chromatography to bind trace levels of impurities and potential contaminants such as DNA, host cell protein, and virus, while allowing the antibody to flow through (Knudsen, H. L., et al., J. Chrom. A 907 (2001) 145-154).

WO 95/16037 reports the purification of anti-EGF-R/anti-CD3 bispecific monoclonal antibodies from hybrid hybridoma performed by protein A and cation exchange chromatography. The separation of antibody monomers from its multimers by use of ion exchange chromatography is reported in EP 1 084 136. U.S. Pat. No. 5,429,746 relates to the application of hydrophobic interaction chromatography combination chromatography to the purification of antibody molecule proteins. An anionic modified microporous membrane for use for the filtration of fluids, particular parenteral or biological liquids contaminated with charged particulates, is reported in U.S. Pat. No. 4,604,208. WO 03/040166 reports a membrane and a device designed for the removal of trace impurities in protein containing streams.

A method for recovering a polypeptide is reported in U.S. Pat. No. 6,716,598. In US 2006/0194953 a method is reported for selectively removing leaked protein A from antibody purified by means of protein A affinity chromatography. The separation of protein monomers from aggregates by use of ion-exchange chromatography is reported in WO 99/62936. Lynch, P. and Londo, T., Gen. Eng. News 11 (1997) 17, report a system for aggregate removal from affinity-purified therapeutic-grade antibody. A two-step purification of a murine monoclonal antibody intended for therapeutic application in man is reported by Jiskoot, W., et al., J. Immunol. Meth. 124 (1989) 143-156.

SUMMARY OF THE INVENTION

The current invention comprises aspects in the field of immunoglobulin purification. It has been found that an anion exchange chromatography step, in which the immunoglobulin in monomeric form can be obtained from an anion exchange material in a flow-through mode, has to be performed in a narrow pH value range of from e.g. pH 7.8 to pH 8.8. Surprisingly a small deviation from this pH value range, e.g., to pH 7.0 or pH 9.0, abolishes this effect. With the method according to the invention it is possible to separate in a single step the immunoglobulin in monomeric form from the immunoglobulin in aggregated form and from immunoglobulin fragments.

One aspect is a method for obtaining an immunoglobulin in monomeric form, wherein the method comprises the following step:

applying an aqueous, buffered solution comprising an immunoglobulin in monomeric and in aggregated form and/or immunoglobulin fragments to an anion exchange chromatography material, whereby the immunoglobulin depleted of immunoglobulin aggregates and immunoglobulin fragments is recovered from the flow-through or supernatant of the anion exchange chromatography material, wherein the aqueous, buffered solution has a pH value of from pH 7.8 to pH 8.8, and thereby an immunoglobulin in monomeric form is obtained. In one embodiment the aqueous, buffered solution has a pH value of from pH 8.0 to pH 8.5. In another embodiment the anion exchange chromatography material is a membrane anion exchange chromatography material. In a further embodiment the anion exchange chromatography material is a strong anion exchange chromatography material. In another embodiment the strong anion exchange chromatography material is Q-sepharose®, i.e. a cross-linked agarose matrix (R) to which quaternary ammonium groups of the formula (CH$_3$)$_3$ are covalently bound. In still another embodiment the method comprises as first step an additional protein A chromatography step or an additional HCIC chromatography step or an additional ion exchange chromatography step.

DETAILED DESCRIPTION OF THE INVENTION

The term "ion exchange material" or grammatical equivalents thereof denotes an immobile matrix that carries covalently bound charged substituents. For overall charge neutrality not covalently bound counter ions are bound to the charged substituents by ionic interaction. The "ion exchange material" has the ability to exchange its not covalently bound counter ions for similarly charged binding partners or ions of the surrounding solution. Depending on the charge of its exchangeable counter ions the "ion exchange material" is referred to as "cation exchange material" or as "anion exchange material". Depending on the nature of the charged group (substituent) the "ion exchange material" is referred to, e.g. in the case of cation exchange materials, as sulfonic acid or sulfopropyl resin (S), or as carboxymethyl resin (CM). Depending on the chemical nature of the charged group/substituent the "ion exchange material" can additionally be classified as strong or weak ion exchange material, depending on the strength of the covalently bound charged substituent. For example, strong cation exchange materials have a sulfonic acid group, preferably a sulfopropyl group, as charged substituent, weak cation exchange materials have a carboxylic acid group, preferably a carboxymethyl group, as charged substituent. Strong anion exchange materials have a quarternary ammonium group, and weak anion exchange materials have a diethylaminoethyl group as charged substituent.

The term "membrane" denotes both a microporous or macroporous membrane. The membrane itself is composed of a polymeric material such as, e.g. polyethylene, polypropylene, ethylene vinyl acetate copolymers, polytetrafluoroethylene, polycarbonate, poly vinyl chloride, polyamides (nylon, e.g. Zetapore™, N$_{66}$ Posidyne™), polyesters, cellulose acetate, regenerated cellulose, cellulose composites, polysulphones, polyethersulfones, polyarylsulphones, polyphenylsulphones, polyacrylonitrile, polyvinylidene fluoride, non-woven and woven fabrics (e.g. Tyvek®), fibrous material, or of inorganic material such as zeolithe, SiO$_2$, Al$_2$O$_3$, TiO$_2$, or hydroxyapatite.

Ion exchange materials are available under different names and from a multitude of companies such as e.g. cation exchange resins Bio-Rex® (e.g. type 70), Chelex® (e.g. type 100), Macro-Prep® (e.g. type CM, High S, 25 S), AG® (e.g. type 50W, MP) all available from BioRad Laboratories, WCX 2 available from Ciphergen, Dowex® MAC-3 available from Dow chemical company, Cellulose CM (e.g. type 23, 52), hyper-D, partisphere available from Whatman plc., Amberlite® IRC (e.g. type 76, 747, 748), Amberlite® GT 73, Toyopearl® (e.g. type SP, CM, 650M) all available from Tosoh Bioscience GmbH, CM 1500 and CM 3000 available from BioChrom Labs, SP-Sepharose™, CM-Sepharose™ available from GE Healthcare, Poros resins available from PerSeptive Biosystems, Asahipak ES (e.g. type 502C), CXpak P, IEC CM (e.g. type 825, 2825, 5025, LG), IEC SP (e.g. type 420N, 825), IEC QA (e.g. type LG, 825) available from Shoko America Inc., 50W cation exchange resin available from Eichrom Technologies Inc., and such as e.g. anion exchange resins like Dowex® 1 available from Dow chemical company, AG® (e.g. type 1, 2, 4), Bio-Rex® 5, DEAE Bio-Gel 1, Macro-Prep® DEAE all available from BioRad Laboratories, anion exchange resin type 1 available from Eichrom Technologies Inc., Source Q, ANX Sepharose® 4, DEAE Sepharose® (e.g. type CL-6B, FF), Q Sepharose®, Capto Q®, Capto S® all available from GE Healthcare, AX-300 available from PerkinElmer, Asahipak ES-502C, AXpak WA (e.g. type 624, G), IEC DEAE all available from Shoko America Inc., Amberlite® IRA-96, Toyopearl® DEAE, TSKgel DEAE all available from Tosoh Bioscience GmbH, Germany. Membrane ion exchange materials are available from different companies such as membrane cation exchange materials Mustang™ C and Mustang™ S available from Pall Corporation, Sartobind™ CM, Sartobind™ S available from Sartorius, and anion exchange membranes, such as Mustang™ Q available from Pall Corporation, Sartobind™ Q available from Sartorius. In a membrane ion exchange material the binding sites can be found at the flow-through pore walls and not hidden within diffusion pores allowing the mass transfer via convection rather than diffusion. In one embodiment the additional chromatography step is a cation exchange chromatography step employing a membrane cation exchange material selected from Sartobind™ CM, or Sartobind™ S, or Mustang™ S, or Mustang™ C. In another embodiment the anion exchange material is a Q-type membrane anion exchange material or Q-type anion exchange column.

A "polypeptide" is a polymer of amino acid residues joined by peptide bonds, whether produced naturally or synthetically. Polypeptides of less than about 20 amino acid residues are referred to as "peptides."

A "protein" is a macromolecule comprising one or more polypeptide chains or at least one polypeptide chain of more than 100 amino acid residues. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "immunoglobulin" and grammatical equivalents thereof denotes a molecule consisting of two light polypeptide chains and two heavy polypeptide chains. Each of the heavy and light polypeptide chains comprises a variable region (generally the amino terminal portion of the polypeptide chains), which contains a binding domain for interaction with an antigen. Each of the heavy and light polypeptide chains also comprises a constant region (generally the carboxyl terminal portion of the polypeptide chains), which may mediate the binding of the antibody to host tissue or factors including various cells of the immune system, some phagocytic cells and a first component (C1q) of the classical complement system. In one embodiment the light and heavy polypeptide chains are chains each consisting of a variable region, i.e. V$_L$ or V$_H$, and a constant region, i.e. of C$_L$ in case of a light polypeptide chain, or of C$_H$1, hinge, C$_H$2, C$_H$3, and optionally C$_H$4 in case of a heavy polypeptide chain. The term "immunoglobulin" also refers to a protein consisting of polypeptides encoded by immunoglobulin genes. The recognized immunoglobulin genes include the different constant region genes as well as the myriad immunoglobulin variable region genes. Immunoglobulins may exist in a variety of forms. Immunoglobulin fragments are e.g. Fv, Fab, and F(ab)$_2$ as well as single chains (e.g. Huston, J. S., et al., Proc. Natl. Acad. Sci. USA 85 (1988) 5879-5883; Bird et al., Science 242 (1988) 423-426; Hood et al., Immunology, Benjamin N.Y., 2nd edition (1984); and Hunkapiller and Hood, Nature 323

(1986) 15-16). In one embodiment of the method according to the invention the immunoglobulin is a monoclonal immunoglobulin.

The term "immunoglobulin in monomeric form" and grammatical equivalents thereof denotes an immunoglobulin molecule not associated with a second immunoglobulin molecule, i.e. neither covalently nor non-covalently bound to another immunoglobulin molecule. The term "immunoglobulin in aggregated form" and grammatical equivalents thereof denotes an immunoglobulin molecule which is associated, either covalently or non-covalently, with at least one additional immunoglobulin molecule or fragment thereof, and which is eluted in a chromatography with a size exclusion chromatography column before the immunoglobulin in monomeric form. The term "in monomeric form" and grammatical equivalents thereof as used within this application not necessarily denotes that 100% of an immunoglobulin molecule are present in monomeric form. It denotes that an immunoglobulin is essentially in monomeric form, i.e. at least 90% of the immunoglobulin are in monomeric from, in one embodiment at least 95% of the immunoglobulin are in monomeric form, in another embodiment at least 98% of the immunoglobulin are in monomeric form, in a further embodiment at least 99% of the immunoglobulin are in monomeric form, and in still another embodiment more than 99% of the immunoglobulin are in monomeric form determined as peak area of a size exclusion chromatogram of the immunoglobulin. The term "in monomeric and in aggregated/fragmented form" denotes a mixture comprising at least immunoglobulin molecules not associated with other immunoglobulin molecules, immunoglobulin molecules associated with other immunoglobulin molecules, and/or parts of other immunoglobulin molecules. In this mixture neither the monomeric form nor the aggregated form nor the fragmented form is present exclusively.

The term "100%" denotes that the amount of components other than a specified component are below the detection limit of the referred to analytical method under the specified conditions.

The terms "90%", "95%", "98%", "99%" denote no exact values but values within the accuracy of the referred to analytical method under the specified conditions.

The term "monomeric immunoglobulin depleted of immunoglobulin aggregates and immunoglobulin fragments" denotes that the monomeric immunoglobulin accounts in certain embodiments for at least 90% by weight, at least 95% by weight, at least 98% by weight, or at least 99% by weight. In turn the immunoglobulin aggregates and immunoglobulin fragments account in certain embodiments for not more than 10% by weight, not more than 5% by weight, not more than 2% by weight, or not more than 1% by weight of the preparation.

General chromatographic methods and their use are known to a person skilled in the art. See for example, Chromatography, 5$^{th}$ edition, Part A: Fundamentals and Techniques, Heftmann, E. (ed.), Elsevier Science Publishing Company, New York, (1992); Advanced Chromatographic and Electromigration Methods in Biosciences, Deyl, Z. (ed.), Elsevier Science BV, Amsterdam, The Netherlands, (1998); Chromatography Today, Poole, C. F., and Poole, S. K., Elsevier Science Publishing Company, New York, (1991); Scopes, Protein Purification: Principles and Practice (1982); Sambrook, J., et al. (eds.), Molecular Cloning: A Laboratory Manual, Second Edition, Cold Spring Harbor Laboratory Press, Cold Spring Harbor, N.Y., 1989; Current Protocols in Molecular Biology, Ausubel, F. M., et al. (eds), John Wiley & Sons, Inc., New York.

For the purification of recombinantly produced immunoglobulins often a combination of different chromatographical steps is employed. Generally a protein A affinity chromatography is followed by one or two additional separation steps. The final purification step is a so called "polishing step" for the removal of trace impurities and contaminants like residual HCP (host cell protein), DNA (host cell nucleic acid), viruses, or endotoxins. For this polishing step only often an anion exchange material in a flow-through mode is used.

The term "flow-through mode" and grammatical equivalents thereof denotes an operation mode of a purification method, in which a solution containing a substance of interest, e.g. an immunoglobulin in monomeric form, to be purified is brought in contact with a stationary phase, in one embodiment a solid phase, whereby the substance of interest does not bind to that stationary phase. As a result the substance of interest is obtained either in the flow-through (if the purification method is a chromatographical method) or the supernatant (if the purification method is a batch method). Substances not of interest, e.g. an immunoglobulin in aggregated form and/or immunoglobulin fragments, which were also present in the solution prior to the bringing into contact with the stationary phase, bind to the stationary phase and are therewith removed from the solution. This does not denote that 100% of the substances not of interest are removed from the solution but essentially 100% of the substances not of interest are removed, in specific embodiments at least 50% of the substances not of interest are removed from the solution, at least 75% of the substances not of interest are removed the from solution, at least 90% of the substances not of interest are removed from the solution, or more than 95% of the substances not of interest are removed from the solution as determined by the peak area of a size exclusion chromatography.

The term "applying to" and grammatical equivalents thereof denotes a partial step of a purification method, in which a solution containing a substance of interest to be purified is brought in contact with a stationary phase. This denotes that a) the solution is added to a chromatographic device in which the stationary phase is located, or b) that a stationary phase is added to the solution. In case a) the solution containing the substance of interest to be purified passes through the stationary phase allowing for an interaction between the stationary phase and the substances in solution. Depending on the conditions, such as e.g. pH, conductivity, salt concentration, temperature, and/or flow rate, some substances of the solution are bound to the stationary phase and, thus, are removed from the solution. Other substances remain in solution. The substances remaining in solution can be found in the flow-through. The "flow-through" denotes the solution obtained after the passage of the chromatographic device. In one embodiment the chromatographic device is a column with chromatography material, or in another embodiment a cassette with membrane chromatography material. The substance of interest not bound to the stationary phase can be recovered from the flow-though by methods familiar to a person of skill in the art, such as e.g. precipitation, salting out, ultrafiltration, diafiltration, lyophilization, affinity chromatography, or solvent volume reduction to obtain a concentrated solution. In case b) the stationary phase is added, e.g. as a powder, to the solution containing the substance of interest to be purified allowing for an interaction between the stationary phase and the substances in solution. After the interaction the stationary phase in removed, e.g. by filtration, and the substance of interest not bound to the stationary phase is obtained in the supernatant.

The term "does not bind to" and grammatical equivalents thereof denotes that a substance of interest, e.g. an immunoglobulin, remains in solution when brought in contact with a stationary phase, e.g. a membrane ion exchange material. This does not denote that 100% of the substance of interest remains in solution but essentially 100% of the substance of interest remains in solution, in specific embodiments at least 50% of the substance of interest remains in solution, at least 65% of the substance of interest remains in solution, at least 80% of the substance of interest remains in solution, at least 90% of the substance of interest remains in solution, or more than 95% of the substance of interest remains in solution as determined by the peak area of a size exclusion chromatography.

The term "buffered" denotes a solution, in which changes of pH due to the addition or release of acidic or basic substances is leveled by a buffer substance. Any buffer substance resulting in such an effect can be used. In one embodiment pharmaceutically acceptable buffer substances are used, such as e.g. phosphoric acid and salts thereof, citric acid and salts thereof, morpholine, 2-(N-morpholino) ethanesulfonic acid and salts thereof, histidine and salts thereof, glycine and salts thereof, or tris (hydroxymethyl) aminomethane (TRIS) and salts thereof. In another embodiment the buffer substance is selected from phosphoric acid and salts thereof, citric acid and salts thereof, or histidine and salts thereof. Optionally the buffered solution may comprise an additional salt, such as e.g. sodium chloride, sodium sulphate, potassium chloride, potassium sulfate, sodium citrate, or potassium citrate.

The term "bind-and-elute mode" and grammatical equivalents thereof denotes an operation mode of a purification method, in which a solution containing a substance of interest to be purified is brought in contact with a stationary phase, in one embodiment with a solid phase, whereby the substance of interest binds to the stationary phase. As a result the substance of interest is retained on the stationary phase whereas substances not of interest are removed with the flow-through or the supernatant. The substance of interest is afterwards eluted from the stationary phase in a second step and thereby recovered from the stationary phase with an elution solution.

Thus, the current invention reports a method for obtaining an immunoglobulin in monomeric form, wherein the method comprises the following step:
applying an aqueous, buffered solution comprising an immunoglobulin in monomeric and in aggregated form and/or immunoglobulin fragments to an anion exchange chromatography material under conditions whereby the immunoglobulin does not bind to the anion exchange chromatography material,
whereby the immunoglobulin in monomeric form is recovered from the flow-through, and
wherein the aqueous, buffered solution has a pH value of from pH 7.8 to pH 8.8.

The term "conditions under which the immunoglobulin in monomeric form does not bind to the anion exchange chromatography material" and grammatical equivalents thereof denotes conditions at which an immunoglobulin in monomeric form is not bound by the anion exchange chromatography material when brought in contact with the anion exchange material. This does not denote that 100% of the immunoglobulin in monomeric form is not bound but essentially 100% of the immunoglobulin in monomeric form is not bound, in specific embodiments at least 50% of the immunoglobulin in monomeric form is not bound, at least 65% of the immunoglobulin in monomeric form is not bound, at least 80% of the immunoglobulin in monomeric form is not bound, at least 90% of the immunoglobulin in monomeric form is not bound, or more than 95% of the immunoglobulin in monomeric form is not bound to the anion exchange material as determined by the peak area in a size exclusion chromatography. In one embodiment the aqueous, buffered solution has a pH value of from pH 7.8 to pH 8.8. In a further embodiment such a condition is a pH value of the aqueous, buffered solution of from pH 8.0 to pH 8.5.

It has now surprisingly been found that an anion exchange chromatography step, in which the immunoglobulin in monomeric form can be obtained from the anion exchange material in a flow-through mode, can be performed in a narrow pH value range of from pH 7.8 to pH 8.8, in one embodiment of from pH 8.0 to pH 8.5. Surprisingly a small deviation of this pH value range, e.g. to pH 7.0 or pH 9.0, reduces this effect. With the method according to the invention it is possible to separate in a single step the immunoglobulin in monomeric form from the immunoglobulin in aggregated form and from immunoglobulin fragments.

The method according to the invention can be employed as a single step method or combined with other steps, such as, e.g., in one embodiment with a protein A chromatography step or a hydrophobic charge induction chromatography step.

In one embodiment the anion exchange chromatography material is a membrane anion exchange chromatography material. It is also advantageous e.g. to remove the bulk of the host cell proteins and culture by-products in a foremost purification step employing an affinity chromatography. The affinity chromatography may e.g. be a protein A affinity chromatography, a protein G affinity chromatography, a hydrophobic charge induction chromatography (HCIC), or a hydrophobic interaction chromatography (HIC, e.g. with phenyl-sepharose, aza-arenophilic resins, or m-aminophenylboronic acid). In one embodiment the method according to the invention comprises a protein A chromatography step or a HCIC chromatography step prior to the anion exchange chromatography step.

In one embodiment of the method according to the invention, wherein the method comprises more than one chromatography step, prior to the application of a solution to one step (or to a subsequent step) of the purification method, parameters, such as e.g. the pH value or the conductivity of the solution, have to be adjusted. In one embodiment the pH value of the aqueous, buffered solution applied to the anion exchange chromatography material is of from pH 7.8 to pH 8.8, in another embodiment of from pH 8.0 to pH 8.5.

The following examples and figures are provided to aid the understanding of the present invention, the true scope of which is set forth in the appended claims. It is understood that modifications can be made in the procedures set forth without departing from the spirit of the invention.

EXAMPLES

Materials and Methods

Conditioned Protein A Eluate:

An anti-CCR5 antibody (hereinafter referred to as mAb CCR5, see e.g. WO 2006/103100) and an anti-CD19 antibody (hereinafter referred to as mAb CD19) were purified in a first step with a protein A affinity chromatography.

The mAb CCR5 was eluted from the protein A column under acidic conditions. Before further processing the pH value of the fraction containing the immunoglobulin was adjusted by dialysis against a buffered solution (e.g. tris (hydroxymethyl) amino-methane (TRIS) or phosphate buffer) to pH values of 7.0, 7.5, 8.0, 8.5, and 9.0. This material is referred to in the following as conditioned protein A eluate of mAb CCR5.

The mAb CD19 was eluted from the protein A column under acidic conditions. Before further processing the pH value of the fraction containing the immunoglobulin was adjusted by dialysis against a buffered solution (e.g. tris (hydroxymethyl) amino-methane (TRIS) or phosphate buffer) to a pH value of pH 8.5. This material is referred to in the following as conditioned protein A eluate of mAb CD19.

Analytical Methods:
Size Exclusion Chromatography:
resin: TSK 3000 (Tosohaas)
column: 300×7.8 mm
flow rate: 0.5 ml/min
buffer: 200 mM potassium phosphate buffer containing 250 mM potassium chloride, adjusted to pH 7.0
wavelength: 280 nm
SDS-PAGE:
LDS sample buffer, fourfold concentrate (4×): 4 g glycerol, 0.682 g TRIS-Base, 0.666 g TRIS-hydrochloride, 0.8 g LDS (lithium dodecyl sulfate), 0.006 g EDTA (ethylene diamin tetra acetic acid), 0.75 ml of a 1% by weight (w/w) solution of Serva Blue G250 in water, 0.75 ml of a 1% by weight (w/w) solution of phenol red, add water to make a total volume of 10 ml.

The solution containing the immunoglobulin was centrifuged to remove debris. An aliquot of the clarified supernatant was admixed with ¼ volumes (v/v) of 4×LDS sample buffer and 1/10 volume (v/v) of 0.5 M 1,4-dithiotreitol (DTT). Then the samples were incubated for 10 min. at 70° C. and protein separated by SDS-PAGE. The NuPAGE® Pre-Cast gel system (Invitrogen Corp.) was used according to the manufacturer's instruction. In particular, 10% NuPAGE® Novex® Bis-TRIS PreCast gels (pH 6.4) and a NuPAGE® MOPS running buffer was used.

Example 1

Figure 1A:
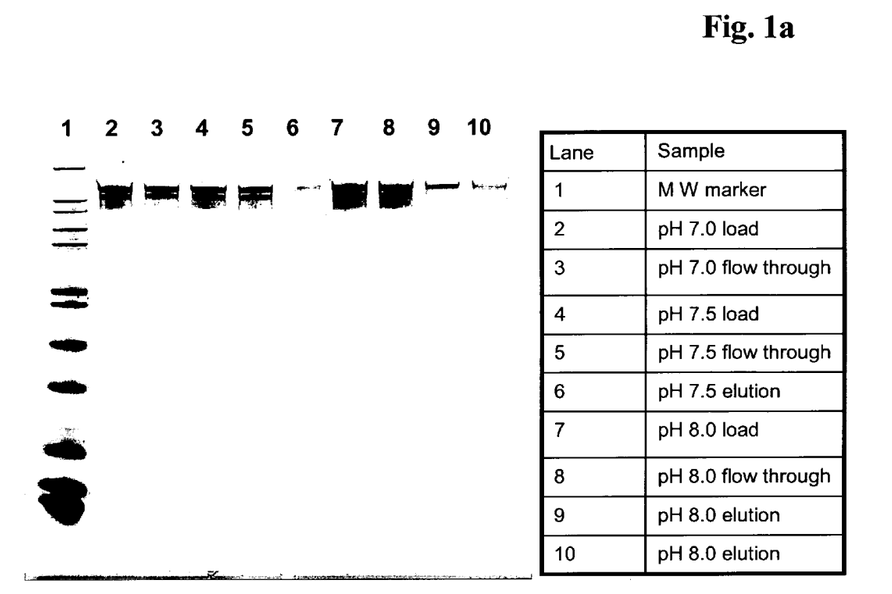
FIG. 1a A solution containing an anti-CCR5 antibody was adjusted to pH 7.0, 7.5 and 8.0 (fractions designated as pH x.x load); 5 mg of protein were each brought in contact with a 15 cm$^2$ membrane adsorber in flow-though mode (fractions designated as pH x.x flow-through). The bound substances were eluted with sodium chloride (fractions designated as pH x.x elution). Fractions were analyzed by SDS-PAGE with Coomassie brilliant blue staining.
Figure 1B:
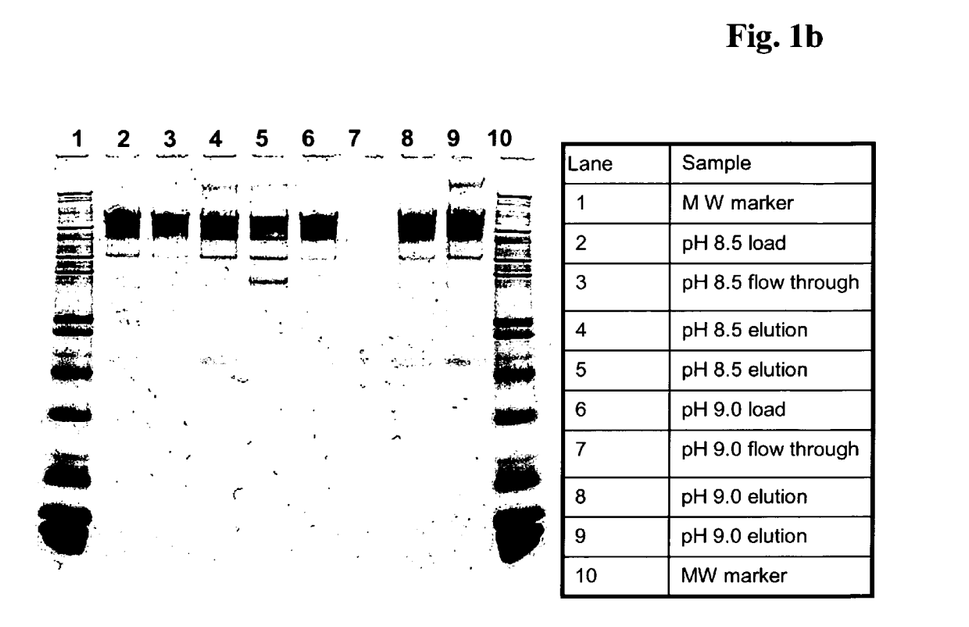
FIG. 1b A solution containing an anti-CCR5 antibody was adjusted to pH 8.5 and 9.0 (fractions designated as pH x.x. load); 5 mg of protein were each brought in contact with a 15 cm² membrane adsorber in flow thought mode (fractions designated as pH x.x flow-through). The bound substances were eluted with sodium chloride (fractions designated as pH x.x. elution). Fractions were analyzed by SDS-PAGE with Coomassie-Staining FIG. 1c Comparison of load and flow-through fractions of an anti-CCR5 antibody containing solution at pH 7.5 (A and B) and load and flow-through fraction at pH 8.5 (C and D) by analytical size exclusion chromatography. Aggregates and fragments can be detected in the flow-through at pH 7.5, but not at pH 8.5
Figure 1C:
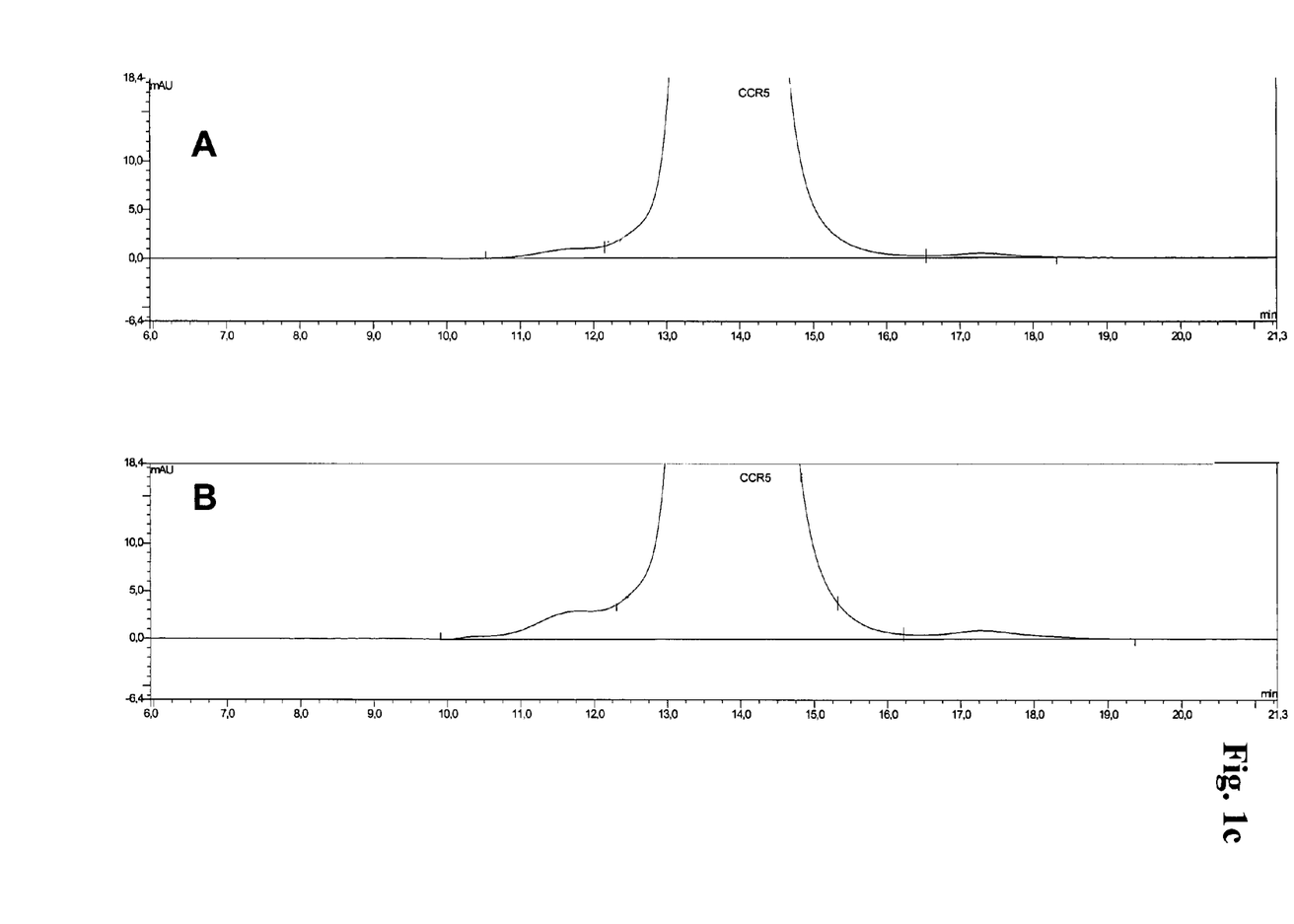

Conditioned protein A eluates of mAb CCR5 with pH 7.0, 7.5, 8.0, 8.5 and 9.0 were each adjusted to a concentration of 1 mg/ml. 5 ml of each solution was applied separately to a regenerated and equilibrated (to the respective pH) Q-membrane adsorber (membrane anion exchange material, membrane area: 15 cm²) in flow-though mode with the help of a chromatographic system. The membrane was afterwards washed with buffer of the correspondent pH. Bound protein was eluted with a salt gradient at the correspondent pH values.

It has been found that mAb CCR5 did not bind at pH 7.0 and 7.5 to the membrane adsorber. Slight binding was achieved between pH 8.0 and 8.5. At pH 9.0 strong binding of the antibody appeared. Analysis of the flow-through and elution fractions by size exclusion chromatography and SDS-PAGE revealed a significant removal of immunoglobulin aggregates and immunoglobulin fragments from the flow-through at pH 8.0 and 8.5. No removal was visible at pH 7.0 and 7.5 and high product losses due to matrix binding occurred at pH 9.0. With conductivity driven elution at pH 8.0 and pH 8.5 fractions enriched with immunoglobulin aggregates and immunoglobulin fragments were obtained.

Example 2

Figure 2A:
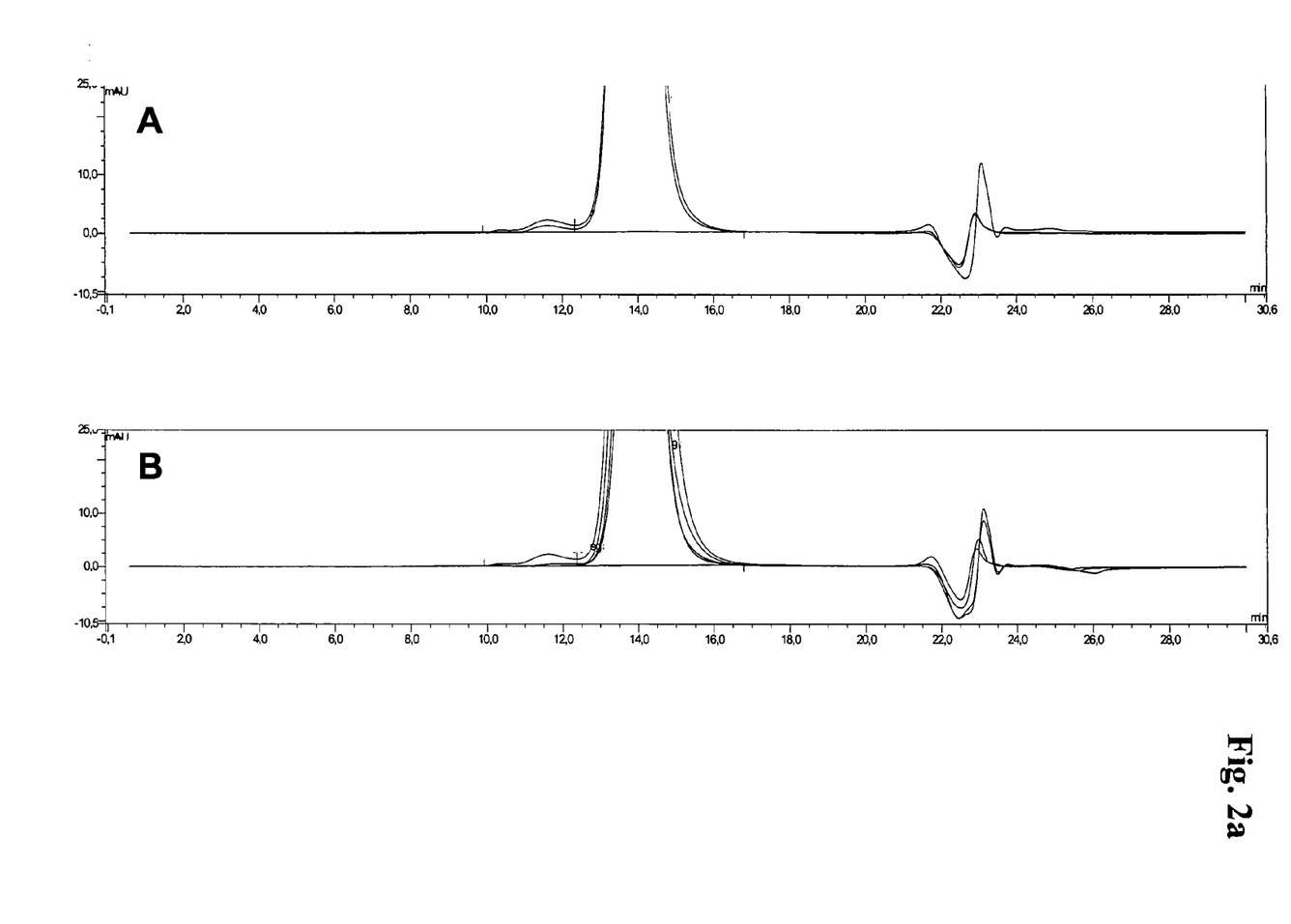
FIG. 2a Overlay showing load and flow-through fraction of a CD19 antibody at pH 7.5 (A) and pH 8.5 (B). Aggregates can be detected in the flow-through at pH 7.5, but not in the flow-through at pH 8.5
Figure 2B:
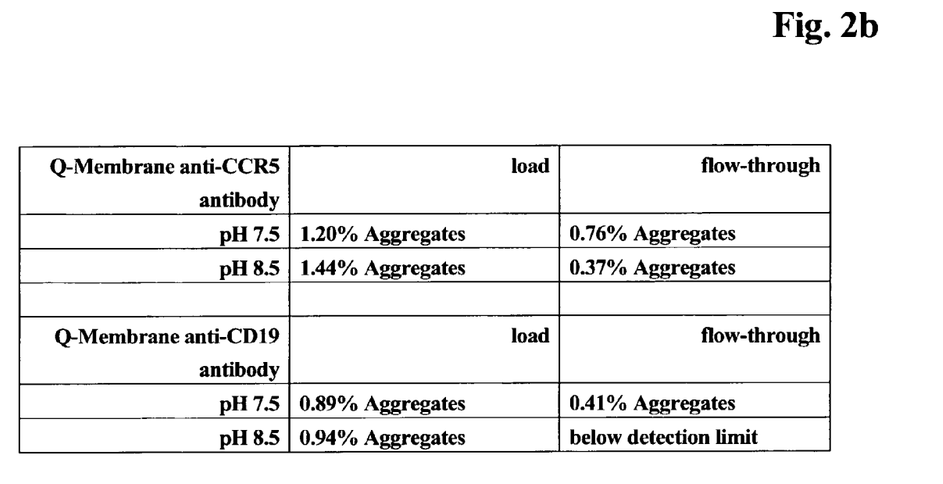
FIG. 2b Table showing the removal of aggregates from anti-CCR5 antibody and anti-CD19 antibody solutions. Reduction in the flow-though is at pH values above pH 7.5, such as pH 8.5.

Conditioned protein A eluates of mAb CD19 with pH 7.0, 7.5, 8.0, 8.5 and 9.0 were each adjusted to a concentration of 1 mg/ml. 5 ml of each solution was applied separately to a regenerated and equilibrated (to the respective pH) Q-membrane adsorber (15 cm²) in flow-though mode with the help of a chromatographic system. The membrane was afterwards washed with buffer of the correspondent pH. Bound protein was eluted with a salt gradient at the correspondent pH values.

It has been found that mAb CD19 did not bind at pH 7.0 and 7.5 to the membrane adsorber. Slight binding was achieved between pH 8.0 and 8.5. At pH 9.0 strong binding of the immunoglobulin appeared. Analysis of the flow-through and elution fractions by size exclusion chromatography and SDS-PAGE revealed a significant removal of immunoglobulin aggregates and immunoglobulin fragments of the immunoglobulin from the product at pH 8.0 and 8.5. No removal was visible at pH 7.0 and pH 7.5 and high product losses due to matrix binding occurred at pH 9.0. With conductivity driven elution at pH 8.0 and pH 8.5 fractions enriched with immunoglobulin aggregates and immunoglobulin fragments were obtained.

Example 3

Figure 3:
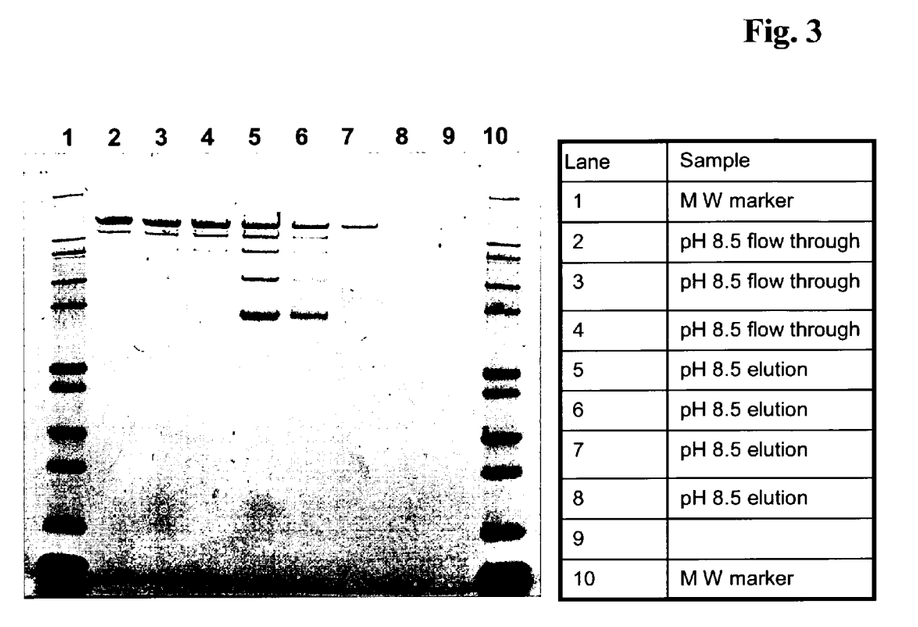
FIG. 3 Scale-up experiment: A solution containing an anti-CCR5 antibody was adjusted to pH 8.5 and 25 mg were pumped through a 75 cm² membrane adsorber (fractions designated as pH x.x flow-through). The bound substances were eluted with sodium chloride (fractions designated as pH x.x. elution). Fractions were analyzed by SDS-PAGE with Coomassie-Staining.

A protein A eluate of mAb CCR5 was conditioned at pH 8.5 and adjusted to a concentration of 1 mg/ml.

25 ml of the solution was applied to a regenerated and equilibrated (to pH 8.5) Q-membrane adsorber (75 cm$^2$ membrane surface area) in flow-through mode with the help of a chromatographic system. The membrane was afterwards washed with buffer of pH 8.5. Bound protein was eluted with a salt gradient at the correspondent pH values.

The result of example 1 could be reproduced at a 5-fold larger scale. The flow-through was depleted from immunoglobulin aggregates and immunoglobulin fragments. Both impurities could be eluted from the membrane adsorber with a salt gradient.

Example 4

Figure 4:
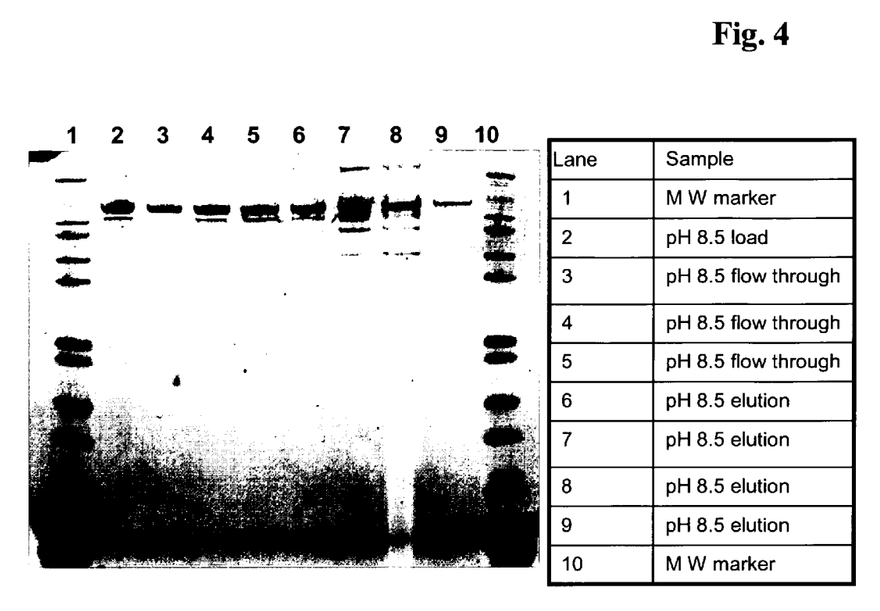
FIG. 4 A solution containing an anti-CCR5 antibody was adjusted to pH 8.5 (fraction designated as pH 8.5 load) and 6 mg protein were pumped through a 1 ml Q-Sepharose® fast-flow anion exchange chromatography column (fractions designated as pH 8.5 flow-through). The column was eluted with sodium chloride (fractions designated as pH 8.5. elution). Fractions were analyzed by SDS-PAGE with Coomassie-Staining.

Conditioned protein A eluate of mAb CCR5 at pH 8.5 was adjusted to a concentration of 1 mg/ml. 6 ml of the solution was applied to a regenerated and equilibrated (to pH 8.5) Q Sepharose® FF in flow-though mode with the help of a chromatographic system. The sepharose was afterwards washed with buffer of the correspondent pH. Bound protein was eluted with a salt gradient at the correspondent pH values.

Analysis of the flow-through and the eluted fractions by size exclusion chromatography and SDS-PAGE revealed a significant removal of immunoglobulin aggregates and immunoglobulin fragments of the immunoglobulin from the product at pH 8.5. With conductivity driven elution at pH 8.0 and pH 8.5 fractions enriched with immunoglobulin aggregates and immunoglobulin fragments were obtained.

The invention claimed is:

1. A method for obtaining an immunoglobulin in monomeric form, wherein the method comprises the following step: applying an aqueous, buffered solution comprising an immunoglobulin in monomeric and in aggregated form and immunoglobulin fragments to a membrane anion exchange chromatography material, wherein the aqueous, buffered solution has a pH value of pH 8.5, whereby the immunoglobulin depleted of immunoglobulin aggregates and immunoglobulin fragments is recovered from the flow-through of the membrane anion exchange chromatography material and thereby an immunoglobulin in monomeric form is obtained.

2. The method according to claim 1, characterized in that said anion exchange chromatography material is a strong anion exchange chromatography material.

3. The method according to any one of the preceding claims, characterized in that said method comprises prior to step a) an additional protein A chromatography step or a HCIC chromatography step.

* * * * *